United States Patent
Mori et al.

(10) Patent No.: US 11,752,073 B2
(45) Date of Patent: Sep. 12, 2023

(54) DENTAL GYPSUM POWDER

(71) Applicant: GC Corporation, Shizuoka (JP)

(72) Inventors: Daizaburo Mori, Tokyo (JP); Kenji Kojima, Tokyo (JP); Masatoshi Yoshinaga, Tokyo (JP)

(73) Assignee: GC Corporation, Shizuoka (JP)

( * ) Notice: Subject to any disclaimer, the term of this patent is extended or adjusted under 35 U.S.C. 154(b) by 688 days.

(21) Appl. No.: 16/967,880

(22) PCT Filed: Oct. 24, 2018

(86) PCT No.: PCT/JP2018/039505
§ 371 (c)(1),
(2) Date: Aug. 6, 2020

(87) PCT Pub. No.: WO2019/159438
PCT Pub. Date: Aug. 22, 2019

(65) Prior Publication Data
US 2021/0045975 A1      Feb. 18, 2021

(30) Foreign Application Priority Data

Feb. 16, 2018 (JP) .................................. 2018-025667

(51) Int. Cl.
*A61K 6/90* (2020.01)
*A61K 6/858* (2020.01)
*C04B 11/00* (2006.01)
*C04B 24/18* (2006.01)
*C04B 24/04* (2006.01)
*A61C 13/34* (2006.01)
*C04B 111/00* (2006.01)
*C04B 103/30* (2006.01)

(52) U.S. Cl.
CPC ................. *A61K 6/90* (2020.01); *A61K 6/858* (2020.01); *C04B 11/00* (2013.01); *C04B 24/04* (2013.01); *C04B 24/18* (2013.01); *A61C 13/34* (2013.01); *C04B 2103/302* (2013.01); *C04B 2111/00836* (2013.01)

(58) Field of Classification Search
CPC .......... A61K 6/858; A61K 6/90; A61C 13/34; C04C 11/00; C04C 24/04; C04C 24/18; C04C 2111/00836; C04C 2103/302
See application file for complete search history.

(56) References Cited

U.S. PATENT DOCUMENTS

| | | |
|---|---|---|
| 2008/0229981 A1 | 9/2008 | Liu et al. |
| 2014/0296369 A1 | 10/2014 | Mori et al. |
| 2019/0142705 A1* | 5/2019 | Mori .................. C04B 40/0028 |
| | | 106/461 |
| 2021/0085433 A1 | 3/2021 | Mori et al. |

FOREIGN PATENT DOCUMENTS

| | | |
|---|---|---|
| JP | S55-154365 | 12/1980 |
| JP | H02-055255 | 2/1990 |
| JP | H05-155731 | 6/1993 |
| JP | 2001-353166 | 12/2001 |
| JP | 2003-049164 | 2/2003 |
| JP | 2004-073609 | 3/2004 |
| JP | 2005-281062 | * 10/2005 |
| JP | 2014-188325 | 10/2014 |
| WO | 2017/208662 | 12/2017 |
| WO | WO 2017-208662 | * 12/2017 |
| WO | 2018/230028 | 12/2018 |

OTHER PUBLICATIONS

Translation for JP 2005-281062, Oct. 13, 2005.*
G. J. Williams el al. "A "Coulter" particle size analysis of denial gypsum materials" Journal of Materials Science Letters 3. p. 93-p. 94 (Jan. 1984).*
International Search Report for PCT/JP2018/039505 dated Dec. 18, 2018.
ACG Materials, Terra Alba, online, ACG Materials, May 29, 2017, URL: http://web.archive.org/web/20170529045319/http://www.acgmateriajs.com/terra-alba/.
G. J. Williams et al, "A "Coulter" particle size analysis of dental gypsum materials" Journal of Materials Science Letters 3, p. 93-p. 94 (Jan. 1984).
"Particle Size Distribution and its Measurement", Masafumi Arakawa, Shikizai, Japan, 1970, vol. 43, pp. 333-343 with partial English translation.

* cited by examiner

*Primary Examiner* — C Melissa Koslow
(74) *Attorney, Agent, or Firm* — IPUSA, PLLC

(57) ABSTRACT

An embodiment according to the present invention provides a dental gypsum powder including a hemihydrate gypsum and a water-reducing agent, wherein the mass ratio of the water-reducing agent to the hemihydrate gypsum is 0.1 to 1%, the content of particles having a particle diameter of 10 μm or less is 15 to 35 volume %, the content of particles having a particle diameter of 20 μm or less is 40 to 55 volume %, and the content of particles having a particle diameter of 30 μm or less is 55 to 75 volume %.

1 Claim, No Drawings

DENTAL GYPSUM POWDER

TECHNICAL FIELD

The present invention relates to a dental gypsum powder.

BACKGROUND ART

Conventionally, a work model, a jaw model, or the like has been used as a gypsum model to reproduce a condition in an oral cavity.

Gypsum models are generally made by injecting a gypsum slurry into a negative mold obtained from an impression in an oral cavity and then curing it with an impression.

In dental clinics and dental engineering laboratories, a gypsum slurry is prepared by pouring a predetermined amount of a gypsum powder and water into a rubber small ball (rubber ball) and then kneading it with a gypsum spatula.

However, when carrying out home-visit medical care, because the gypsum slurry preparation method described above needs to prepare a wide variety of tools, which is complicated, a simpler gypsum slurry preparation method has been demanded.

Patent Document 1 discloses a method of preparing a gypsum slurry in which a dental gypsum powder and water are sealed in a bottle and then the bottle is shaken. ON this occasion, the dental gypsum powder contains a hemihydrate gypsum and a polycarboxylate water reducing agent, and the mass ratio of the polycarboxylate water reducing agent to the hemihydrate gypsum is not less than 0.05% and not more than 0.8%.

PRIOR ART DOCUMENTS

Patent Documents

Patent Document 1: WO 2017/208662

SUMMARY OF THE INVENTION

Problem to be Solved by the Invention

Here, in order to increase the strength of a gypsum hardened body, when preparing a gypsum slurry, it is necessary to shake until a dental gypsum powder and water are uniformly mixed. However, shortening the shaking period is demanded.

Accordingly, one aspect of the present invention is to provide a dental gypsum powder capable of increasing the strength of a gypsum hardened body even when the shaking period in preparing a gypsum slurry is shortened.

Means for Solving the Problem

One embodiment of the present invention is intended to provide a dental gypsum powder that includes a hemihydrate gypsum and a water reducing agent, wherein a mass ratio of the water reducing agent to the hemihydrate gypsum is not less than 0.1% and not more than 1%, wherein a particle content of a particle with a particle size of 10 μm or less is not less than 15% by volume and not more than 35% by volume, wherein a particle content of a particle with a particle size of 20 μm or less is not less than 40% by volume and not more than 55% by volume, and wherein a particle content of a particle with a particle size of 30 μm or less is not more than 55% by volume and not more than 75% by volume.

Effect of the Invention

According to an embodiment of the invention, a dental gypsum powder capable of increasing the strength of a gypsum hardened body can be provided even when shaking period in preparing a gypsum slurry is shortened.

EMBODIMENTS FOR IMPLEMENTING THE INVENTION

Hereinafter, an embodiment for carrying out the present invention will be described. The invention is not limited to the following embodiments, and various modifications and substitutions can be made to the following embodiments without departing from the scope of the claims.

Dental Gypsum Powder

A dental gypsum powder of this embodiment includes hemihydrate gypsum and semi-hydrate gypsum.

Here, the dental gypsum powder according to the present embodiment can be sealed in a bottle with water as described below, and the bottle can be shaken to prepare a gypsum slurry.

The mass ratio of the water reducing agent to the hemihydrate gypsum in the dental gypsum powder according to the present embodiment is preferably 0.1% or more and 1% or less, and 0.2% or more and 0.5% or less. If the mass ratio of the water reducing agent to the hemihydrate gypsum in the dental gypsum powder is less than 0.1%, the strength of the gypsum hardened body cannot be increased unless the shaking period in preparing the gypsum slurry is prolonged. On the other hand, if the mass ratio of the water reducing agent to the hemihydrate gypsum in the dental gypsum powder exceeds 1%, curing is significantly delayed, and thus the strength of the gypsum hardened body cannot be increased.

The particle size of the dental gypsum powder according to the present embodiment is not less than 10 μm. The particle content is preferably not less than 15% by volume and not more than 35% by volume, and not less than 20% by volume and not more than 30% by volume. If the particle size of the dental gypsum powder is less than 15% by volume or more than 35% by volume, the strength of the gypsum hardened body cannot be increased unless the shaking period when preparing the gypsum slurry is increased.

The particle size of the dental gypsum powder according to the present embodiment is 20 μm or less, and the particle content is preferably not less than 40% by volume and not more than 55% by volume, and not less than 45% by volume and not more than 55% by volume. When the particle size of the dental gypsum powder is 20 μm or less and the particle content is less than 40% by volume or more than 55% by volume, the strength of the gypsum hardened body cannot be increased unless the shaking period when preparing the gypsum slurry is increased.

The particle size of the dental gypsum powder according to the present embodiment is 30 μm or less, and the particle content of the dental gypsum powder is preferably not less than 55% and not more than 75% by volume, and not less than 58% and not more than 72% by volume. When the particle size of the dental gypsum powder is 30 μm or less and the particle size is less than 55% by volume or greater than 75% by volume, the strength of the gypsum hardened body cannot be increased unless the shaking period when preparing the gypsum slurry is increased.

The particle content having a particle size of 67.5 μm or less in the dental gypsum powder according to the present embodiment is preferably not less than 80% and not more than 96% by volume. If the particle content having the particle size of 67.5 μm or less in the dental gypsum powder according to the present embodiment is 80% or more and 96% or less, the strength of the gypsum hardened body is further increased when the shaking period in preparing the gypsum slurry is shortened.

Hemihydrate Gypsum

As hemihydrate gypsum, α-hemihydrate gypsum or β-hemihydrate gypsum may be used, and the α-hemihydrate gypsum may be combined with the β-hemihydrate gypsum.

Water Reducing Agent

Examples of the water reducing agent include, but are not particularly limited to, water reducing agent of denaturing polycarboxylic acid type, water reducing agent of polyether/polycarboxylic acid type, water reducing agent of melamine sulfonic acid type, water reducing agent of naphthalene sulfonic acid type, water reducing agent of lignin sulfonic acid type, and the like, which may be used in combination with two or more kinds of the agents.

Examples of commercially available modified polycarboxylic acid water reducing agents include MELFLUX AP 101F (manufactured by SKW East Asia Ltd.).

Examples of commercially available polyether-polycarboxylic acid water reducing agents include MELFLUX 2641 F, MELFLUX 2651 F, MELFLUX 5581 F, MELFLUX 4930 F, MELFLUX 6681 F, and MELFLUX BF 11 F (manufactured by SKW East Asia Ltd.).

Examples of commercially available melamine sulfonic acid water reducing agents include MELMENT F10M and MELMENT F4000 (manufactured by SKW East Asia Ltd.).

Examples of commercially available naphthalene sulfonic acid water reducing agents include mitey 100 (manufactured by Kao Corporation) and POWERCON-100 (manufactured by SKW East Asia Co., Ltd.).

Examples of commercially available lignin-sulfonic acid water reducing agents include LIGNOSULFONATE ARBO N18, LIGNOSULFONATE ARBO S01P, and NORLIG SA (manufactured by SKW East Asia Co., Ltd.).

Dihydrate Gypsum

The dental gypsum powder of this embodiment preferably further contains dihydrate gypsum. This facilitates curing of the gypsum slurry.

The gypsum may be gypsum or chemical gypsum, and the gypsum may be combined with chemical gypsum.

A mass ratio of the dihydrate gypsum to the hemihydrate gypsum in the dental gypsum powder according to the present embodiment is preferably not less than 0.2% and not more than 4%, and the mass ratio of the dihydrate gypsum is further preferably not less than 0.3% and not more than 2%. When the mass ratio of dihydrate gypsum to hemihydrate gypsum in the dental gypsum powder according to the present embodiment is 0.2% by mass or more, curing of the gypsum slurry can be promoted, and when the mass ratio is 4% or less, curing expansion can be inhibited.

Potassium Sulfate

The dental gypsum powder of this embodiment preferably further contains potassium sulfate. Thus, curing expansion can be inhibited.

The mass ratio of potassium sulfate to hemihydrate gypsum in the dental gypsum powder according to the present embodiment is preferably 0.1% or more and 3% or less, and further preferably 0.3% or more and 2% or less. When the mass ratio of potassium sulfate to hemihydrate gypsum in the dental gypsum powder according to the present embodiment is not less than 0.1% and not more than 3%, curing of the gypsum slurry can be promoted.

Other Ingredients

The dental gypsum powder of this embodiment may further contain a curing inhibitor, a curing retarder, a coloring agent, a lightweight agent, and the like.

Examples of curing inhibitors include sodium sulfate, potassium tartrate, and the like.

Examples of curing retarders include salts such as citrates, borates, acetates, and the like; water soluble polymers such as starch, gum arabic, carboxymethylcellulose, gelatin, and the like.

Preparation of Gypsum Slurry

The gypsum slurry can be prepared by sealing a dental gypsum powder and water in a bottle and shaking the bottle in accordance with this embodiment.

The mass ratio of water to the dental gypsum powder in this embodiment is preferably not less than 0.18 and not more than 0.30, and is further preferably not less than 0.20 and not more than 0.25. When the mass ratio of water to the dental gypsum powder in this embodiment is not less than 0.18, the flowability of the gypsum slurry increases, and when the mass ratio is not more than 0.30, the strength of the gypsum hardened body increases.

EXAMPLE

Hereinafter, examples of the present invention will be described, but the present invention is not limited to the examples.

Preparation of Dental Gypsum Powder

The α-hemihydrate gypsum, potassium sulfate, gypsum dihydrate, and water reducing agent were mixed in a pot mill with a predetermined combination (see Table 1) for a predetermined period of time (see Table 1) to prepare gypsum powder for dental use.

The meanings of abbreviations of water reducing agents in Table 1 are as follows.

Mighty 100: Naphthalene sulfonic acid water reducing agent (manufactured by Kao Corporation)

MELFLUX 2651F: Water reducing agent for polyether/polycarboxylic acid (made by SKW East Asia Ltd.) MELMENT F10M: melamine sulfonate water reducing agent (SKW East Asia Ltd.)

Particle Size Distribution of Dental Gypsum Powder

After the dental gypsum powder was dispersed in isobutyl alcohol without using ultrasonic waves, the particle size (spherical equivalent diameter) distribution of the dental gypsum powder was measured on a volume basis under the following measurement conditions using a laser diffraction/scattering particle size distribution measuring device, Partica LA-950V2 (manufactured by Horiba, Ltd.).

Dental gypsum powder refractive index: 1.550
Refractive index of isobutyl alcohol: 1.396
Circulation: Present
Agitation: None
Data capture count: 5000

Preparation of Gypsum Slurry

A dental gypsum powder and water were sealed in a 200 mL raborane styrene rod bottle (manufactured by AS ONE Corporation) as a polystyrene cylindrical bottle at a predetermined mass ratio (see Table 1) for a predetermined period of time (see Table 1) to prepare a gypsum slurry.

The shaking period in Table 1 means the period of time until the residue of the dental gypsum powder in the bottle is eliminated and the dental gypsum powder and water are uniformly mixed.

Strength of Gypsum Hardened Body

The strength of the gypsum hardened gypsum after 60 minutes from the start of shaking when preparing the gypsum slurry was measured according to the method specified in JIS T6605, "Dental Hard Gypsum."

Table 1 shows the evaluation results of the strength of the gypsum hardened body.

Because the dental gypsum powder of Comparative Example 2 has a particle content of 58.2% by volume with a particle size of 20 μm or lower and a particle content of 88.9% by volume with a particle size of 30 μm or less, the shaking period becomes 30 seconds.

Because the dental gypsum powder of Comparative Example 3 has a particle content of 4.7% by volume with a particle size of 10 μm or less and a particle content of 21.0% by volume with a particle size of 20 μm or less, the shaking period becomes 60 seconds.

Because the dental gypsum powder of Comparative Example 4 has a particle content of 60.8% by volume with a particle size of 20 μm or less and a particle content of 87.4% by volume with a particle size of 30 μm or less, the shaking period becomes 60 seconds.

Because the dental gypsum powder of Comparative Examples 5 and 6 contains 85.4% by volume and 79.1% by volume of particles having a particle size of 30 μm or less, the shaking period becomes 60 seconds.

This international application claims priority to Japanese Patent Application No. 2018-025667, filed Feb. 16, 2018, and the entire contents of Japanese Patent Application No. 2018-025667 are incorporated herein by reference.

The invention claimed is:
1. A dental gypsum powder, comprising:
a hemihydrate gypsum; and
a water reducing agent,
wherein a mass ratio of the water reducing agent to the hemihydrate gypsum is not less than 0.1% and not more than 1%,

TABLE 1

|  | EXAMPLE ||||||  COMPARATIVE EXAMPLE ||||||
|  | 1 | 2 | 3 | 4 | 5 | 6 | 1 | 2 | 3 | 4 | 5 | 6 |
|---|---|---|---|---|---|---|---|---|---|---|---|---|
| COMPOSITION OF DENTAL GYPSUM POWDER [VOL %] |||||||||||||
| α-HEMIHYDRATE GYPSUM | 100 | 100 | 100 | 100 | 100 | 100 | 100 | 100 | 100 | 100 | 100 | 100 |
| POTASSIUM SULFATE | 0.1 | 0.1 | 0.1 | 0.1 | 0.1 | 0.1 | 0.1 | 0.1 | 0.1 | 0.1 | 0.1 | 0.1 |
| DIHYDRATE GYPSUM | 0.3 | 0.3 | 0.3 | 0.3 | 0.3 | 0.3 | 0.3 | 0.3 | 0.3 | 0.3 | 0.3 | 0.3 |
| MIGHTY 100 |  | 0.3 |  |  |  |  |  |  |  | 0.2 |  |  |
| MELFLUX 2651F | 0.4 |  |  |  | 0.2 | 0.2 |  | 0.2 |  |  | 0.2 |  |
| MELMENT F10M |  |  | 0.5 | 0.8 |  |  |  |  | 0.5 |  |  | 0.2 |
| MANUFACTURING CONDITION OF DENTAL GYPSUM POWDER |||||||||||||
| MIXING TIME [MINUTES] | 75 | 60 | 45 | 60 | 60 | 60 | 75 | 60 | 10 | 60 | 45 | 45 |
| PARTICLE SIZE DISTRIBUTION OF DENTAL GYPSUM POWDER [VOLUME %] |||||||||||||
| PARTICLE SIZE 10 μm OR LESS | 26.6 | 20.7 | 18.4 | 22.3 | 21.3 | 21.0 | 23.0 | 19.2 | 4.7 | 20.2 | 16.3 | 13.0 |
| PARTICLE SIZE 20 μm OR LESS | 48.4 | 48.0 | 47.4 | 48.8 | 46.2 | 46.6 | 45.5 | 58.2 | 21.0 | 60.8 | 54.0 | 41.6 |
| PARTICLE SIZE 30 μm OR LESS | 60.5 | 64.0 | 62.9 | 64.7 | 61.1 | 62.3 | 59.0 | 88.9 | 61.8 | 87.4 | 85.4 | 79.1 |
| PARTICLE SIZE 67.5 μm OR LESS | 83.2 | 92.5 | 91.7 | 94.0 | 89.9 | 91.4 | 86.1 | 97.0 | 85.8 | 94.9 | 95.1 | 93.5 |
| PREPARATION CONDITION OF GYPSUM SLURRY |||||||||||||
| MASS RATIO OF WATER TO GYPSUM POWDER | 0.22 | 0.20 | 0.25 | 0.25 | 0.25 | 0.25 | 0.25 | 0.25 | 0.25 | 0.25 | 0.25 | 0.25 |
| SHAKING PERIOD [SECOND] | 15 | 20 | 15 | 10 | 10 | 10 | >60 | 30 | 60 | 60 | 60 | 60 |
| EVALUATION RESULT OF GYPSUM HARDENED BODY |||||||||||||
| STRENGTH [MPa] | 52 | 47 | 39 | 38 | 40 | 38 | — | 40 | 38 | 41 | 35 | 30 |

From Table 1, it can be seen that the dental gypsum powder of Examples 1 to 6 has a high strength of gypsum hardened body even when the shaking period is 10 to 20 seconds.

On the other hand, the dental gypsum powder of Comparative Example 1 does not contain a water reducing agent and thus has a shaking period beyond 60 seconds.

wherein a particle content of a particle with a particle size of 10 μm or less is not less than 15% by volume and not more than 35% by volume, wherein a particle content of a particle with a particle size of 20 μm or less is not less than 40% by volume and not more than 55% by volume, and wherein a particle content of a particle with a particle size of 30 μm or less is not less than 55% by volume and not more than 75% by volume.

* * * * *